US00RE47244E

(19) United States
(12) Reissued Patent
Kiani et al.

(10) Patent Number: US RE47,244 E
(45) Date of Reissued Patent: Feb. 19, 2019

(54) ALARM SUSPEND SYSTEM

(71) Applicant: MASIMO CORPORATION, Irvine, CA (US)

(72) Inventors: Massi Joe E. Kiani, Laguna Niguel, CA (US); Steve L. Cebada, Mission Viejo, CA (US); Gregory A. Olsen, Trabuco Canyon, CA (US)

(73) Assignee: MASIMO CORPORATION, Irvine, CA (US)

(21) Appl. No.: 15/583,935

(22) Filed: May 1, 2017

Related U.S. Patent Documents

Reissue of:
(64) Patent No.: 9,153,121
Issued: Oct. 6, 2015
Appl. No.: 14/469,426
Filed: Aug. 26, 2014

U.S. Applications:
(63) Continuation of application No. 14/036,496, filed on Sep. 25, 2013, now Pat. No. 8,847,740, which is a
(Continued)

(51) Int. Cl.
*G08B 5/22* (2006.01)
*G08B 25/00* (2006.01)
(Continued)

(52) U.S. Cl.
CPC ..... *A61B 5/1455* (2013.01); *A61B 5/6826* (2013.01); *A61B 5/6838* (2013.01);
(Continued)

(58) Field of Classification Search
CPC ... A61B 5/1455; A61B 5/6826; A61B 5/6838; A61B 5/746; A61B 256/0276; G08B 25/001; G08B 5/22
(Continued)

(56) References Cited

U.S. PATENT DOCUMENTS 4,639,718 A * 1/1987 Gasper ..... G05D 21/02 210/739
4,653,498 A 3/1987 New et al.
(Continued)

FOREIGN PATENT DOCUMENTS

WO WO 2005/087097 9/2005
WO WO 2010/014743 2/2010

OTHER PUBLICATIONS

US 9,579,050, 02/2017, Al-Ali (withdrawn)
(Continued)

*Primary Examiner* — Ovidio Escalante
(74) *Attorney, Agent, or Firm* — Knobbe, Martens, Olson & Bear LLP

(57) ABSTRACT

An alarm suspend system utilizes an alarm trigger responsive to physiological parameters and corresponding limits on those parameters. The parameters are associated with both fast and slow treatment times corresponding to length of time it takes for a person to respond to medical treatment for out-of-limit parameter measurements. Audible and visual alarms respond to the alarm trigger. An alarm silence button is pressed to silence the audible alarm for a predetermined suspend time. The audible alarm is activated after the suspend time has lapsed. Longer suspend times are associated with slow treatment parameters and shorter suspend times are associated with fast treatment parameters.

26 Claims, 5 Drawing Sheets

Related U.S. Application Data continuation of application No. 13/476,725, filed on May 21, 2012, now Pat. No. 8,547,209, which is a continuation of application No. 12/510,982, filed on Jul. 28, 2009, now Pat. No. 8,203,438.

(60) Provisional application No. 61/084,615, filed on Jul. 29, 2008.

(51) Int. Cl.
*A61B 5/00* (2006.01)
*A61B 5/1455* (2006.01)
*G08B 25/01* (2006.01)

(52) U.S. Cl.
CPC ..... *A61B 5/746* (2013.01); *G08B 25/01* (2013.01); *A61B 2560/0276* (2013.01); *G08B 5/22* (2013.01)

(58) Field of Classification Search
USPC .. 340/511, 517, 573.1, 539.12, 286.07, 527; 600/310, 316, 322–324, 336, 344, 507, 600/301, 320
See application file for complete search history.

(56) References Cited

U.S. PATENT DOCUMENTS 4,960,128 A 10/1990 Gordon et al.
4,964,408 A 10/1990 Hink et al.
5,041,187 A 8/1991 Hink et al.
5,069,213 A 12/1991 Polczynski
5,111,817 A 5/1992 Clark et al.
5,163,438 A 11/1992 Gordon et al.
5,226,417 A 7/1993 Swedlow et al.
5,253,645 A 10/1993 Friedman et al.
5,253,646 A 10/1993 Delpy et al.
5,319,355 A 6/1994 Russek
5,319,363 A * 6/1994 Welch ..... H04Q 9/00 340/12.3
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,561,275 A 10/1996 Savage et al.
5,562,002 A 10/1996 Lalin
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,685,299 A 11/1997 Diab et al.
D393,830 S 4/1998 Tobler et al.
5,743,262 A 4/1998 Lepper, Jr. et al.
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,876,348 A 3/1999 Sugo et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,995,855 A 11/1999 Kiani et al.
5,997,343 A 12/1999 Mills et al.
6,002,952 A 12/1999 Diab et al.
6,005,658 A 12/1999 Kaluza et al.
6,011,986 A 1/2000 Diab et al.
6,027,452 A 2/2000 Flaherty et al.
6,036,642 A 3/2000 Diab et al.
6,045,509 A 4/2000 Caro et al.
6,050,951 A 4/2000 Friedman et al.
6,067,462 A 5/2000 Diab et al.
6,081,735 A 6/2000 Diab et al.
6,088,607 A 7/2000 Diab et al.
6,110,522 A 8/2000 Lepper, Jr. et al.
6,124,597 A 9/2000 Shehada
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,190,325 B1 2/2001 Narimatsu
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,285,896 B1 9/2001 Tobler et al.
6,301,493 B1 10/2001 Marro et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,430,437 B1 8/2002 Marro
6,430,525 B1 8/2002 Weber et al.
6,463,311 B1 10/2002 Diab
6,470,199 B1 10/2002 Kopotic et al.
6,501,975 B2 12/2002 Diab et al.
6,505,059 B1 1/2003 Kollias et al.
6,515,273 B2 2/2003 Al-Ali
6,519,487 B1 2/2003 Parker
6,525,386 B1 2/2003 Mills et al.
6,526,300 B1 2/2003 Kiani et al.
6,541,756 B2 4/2003 Schulz et al.
6,542,764 B1 4/2003 Al-Ali et al.
6,553,242 B1 4/2003 Sarussi
6,580,086 B1 6/2003 Schulz et al.
6,584,336 B1 6/2003 Ali et al.
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,639,668 B1 10/2003 Trepagnier

(56) References Cited

U.S. PATENT DOCUMENTS 6,640,116 B2 10/2003 Diab
6,643,530 B2 11/2003 Diab et al.
6,645,155 B2 11/2003 Inukai et al.
6,650,917 B2 11/2003 Diab et al.
6,654,624 B2 11/2003 Diab et al.
6,658,276 B2 * 12/2003 Kianl et al. ..... 600/322
6,661,161 B1 12/2003 Lanzo et al.
6,671,531 B2 12/2003 Al-Ali et al.
6,678,543 B2 1/2004 Diab et al.
6,684,090 B2 1/2004 Ali et al.
6,684,091 B2 1/2004 Parker
6,697,656 B1 2/2004 Al-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,721,582 B2 4/2004 Trepagnier et al.
6,721,585 B1 4/2004 Parker
6,725,075 B2 4/2004 Al-Ali
6,728,560 B2 4/2004 Kollias et al.
6,735,459 B2 5/2004 Parker
6,745,060 B2 6/2004 Diab et al.
6,754,516 B2 6/2004 Mannheimer
6,760,607 B2 7/2004 Al-Ali
6,770,028 B1 8/2004 Ali et al.
6,771,994 B2 8/2004 Kiani et al.
6,792,300 B1 9/2004 Diab et al.
6,813,511 B2 11/2004 Diab et al.
6,816,741 B2 11/2004 Diab
6,822,564 B2 11/2004 Al-Ali
6,826,419 B2 11/2004 Diab et al.
6,830,711 B2 12/2004 Mills et al.
6,850,787 B2 2/2005 Weber et al.
6,850,788 B2 2/2005 Al-Ali
6,852,083 B2 2/2005 Caro et al.
6,861,639 B2 3/2005 Al-Ali
6,898,452 B2 5/2005 Al-Ali et al.
6,920,345 B2 7/2005 Al-Ali et al.
6,931,268 B1 8/2005 Kiani-Azarbayjany et al.
6,934,570 B2 8/2005 Kiani et al.
6,939,305 B2 9/2005 Flaherty et al.
6,943,348 B1 9/2005 Coffin IV
6,950,687 B2 9/2005 Al-Ali
6,961,598 B2 11/2005 Diab
6,970,792 B1 11/2005 Diab
6,979,812 B2 12/2005 Al-Ali
6,985,764 B2 1/2006 Mason et al.
6,993,371 B2 1/2006 Kiani et al.
6,996,427 B2 2/2006 Ali et al.
6,999,904 B2 2/2006 Weber et al.
7,003,338 B2 2/2006 Weber et al.
7,003,339 B2 2/2006 Diab et al.
7,015,451 B2 3/2006 Dalke et al.
7,024,233 B2 4/2006 Ali et al.
7,027,849 B2 4/2006 Al-Ali
7,030,749 B2 4/2006 Al-Ali
7,039,449 B2 5/2006 Al-Ali
7,041,060 B2 5/2006 Flaherty et al.
7,044,918 B2 5/2006 Diab
7,067,893 B2 6/2006 Mills et al.
7,096,052 B2 8/2006 Mason et al.
7,096,054 B2 8/2006 Abdul-Hafiz et al.
7,123,950 B2 10/2006 Mannheimer
7,132,641 B2 11/2006 Schulz et al.
7,142,901 B2 11/2006 Kiani et al.
7,149,561 B2 12/2006 Diab
7,186,966 B2 3/2007 Al-Ali
7,190,261 B2 3/2007 Al-Ali
7,215,984 B2 5/2007 Diab
7,215,986 B2 5/2007 Diab
7,221,971 B2 5/2007 Diab
7,225,006 B2 5/2007 Al-Ali et al.
7,225,007 B2 5/2007 Al-Ali
RE39,672 E 6/2007 Shehada et al.
7,239,905 B2 7/2007 Kiani-Azarbayjany et al.
7,245,953 B1 7/2007 Parker
7,254,429 B2 8/2007 Schurman et al.
7,254,431 B2 8/2007 Al-Ali
7,254,433 B2 8/2007 Diab et al.
7,254,434 B2 8/2007 Schulz et al.
7,272,425 B2 9/2007 Al-Ali
7,274,955 B2 9/2007 Kiani et al.
D554,263 S 10/2007 Al-Ali
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,471,969 B2 12/2008 Diab et al.
7,471,971 B2 12/2008 Diab et al.
7,483,729 B2 1/2009 Al-Ali et al.
7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,526,328 B2 4/2009 Diab et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,596,398 B2 9/2009 Al-Ali et al.
7,618,375 B2 11/2009 Flaherty
D606,659 S 12/2009 Kiani et al.
7,647,083 B2 1/2010 Al-Ali et al.
D609,193 S 2/2010 Al-Ali et al.
D614,305 S 4/2010 Al-Ali et al.
RE41,317 E 5/2010 Parker
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,791,155 B2 9/2010 Diab
7,801,581 B2 9/2010 Diab
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,865,222 B2 1/2011 Weber et al.
7,873,497 B2 1/2011 Weber et al.
7,880,606 B2 2/2011 Al-Ali
7,880,626 B2 2/2011 Al-Ali et al.

(56) References Cited

U.S. PATENT DOCUMENTS 7,891,355 B2 2/2011 Al-Ali et al.
7,894,868 B2 2/2011 Al-Ali et al.
7,899,507 B2 3/2011 Al-Ali et al.
7,899,518 B2 3/2011 Trepagnier et al.
7,904,132 B2 3/2011 Weber et al.
7,909,772 B2 3/2011 Popov et al.
7,910,875 B2 3/2011 Al-Ali
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,976,472 B2 7/2011 Kiani
7,988,637 B2 8/2011 Diab
7,990,382 B2 8/2011 Kiani
7,991,446 B2 8/2011 Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,727 B2 10/2011 Schurman et al.
8,036,728 B2 10/2011 Diab et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,126,528 B2 2/2012 Diab et al.
8,123,572 B2 3/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,203,438 B2 * 6/2012 Kiani et al. ..... 340/286.07
8,203,704 B2 6/2012 Merritt et al.
8,204,566 B2 6/2012 Schurman et al.
8,219,172 B2 7/2012 Schurman et al.
8,224,411 B2 7/2012 Al-Ali et al.
8,228,181 B2 7/2012 Al-Ali
8,229,533 B2 7/2012 Diab et al.
8,233,955 B2 7/2012 Al-Ali et al.
8,244,325 B2 8/2012 Al-Ali et al.
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,274,360 B2 9/2012 Sampath et al.
8,301,217 B2 10/2012 Al-Ali et al.
8,306,596 B2 11/2012 Schurman et al.
8,310,336 B2 11/2012 Muhsin et al.
8,315,683 B2 11/2012 Al-Ali et al.
RE43,860 E 12/2012 Parker
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,364,223 B2 1/2013 Al-Ali et al.
8,364,226 B2 1/2013 Diab et al.
8,374,665 B2 2/2013 Lamego
8,385,995 B2 2/2013 Al-Ali et al.
8,385,996 B2 2/2013 Smith et al.
8,388,353 B2 3/2013 Kiani et al.
8,399,822 B2 3/2013 Al-Ali
8,401,602 B2 3/2013 Kiani
8,401,607 B2 3/2013 Mannheimer
8,405,608 B2 3/2013 Al-Ali et al.
8,414,499 B2 4/2013 Al-Ali et al.
8,418,524 B2 4/2013 Al-Ali
8,423,106 B2 4/2013 Lamego et al.
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellott et al.
8,471,713 B2 6/2013 Poeze et al.
8,473,020 B2 6/2013 Kiani et al.
8,483,787 B2 7/2013 Al-Ali et al.
8,489,364 B2 7/2013 Weber et al.
8,498,684 B2 7/2013 Weber et al.
8,504,128 B2 8/2013 Blank et al.
8,509,867 B2 8/2013 Workman et al.
8,515,509 B2 8/2013 Bruinsma et al.
8,523,781 B2 9/2013 Al-Ali
8,529,301 B2 9/2013 Al-Ali et al.
8,532,727 B2 9/2013 Ali et al.
8,532,728 B2 9/2013 Diab et al.
D692,145 S 10/2013 Al-Ali et al.
8,547,209 B2 * 10/2013 Kiani et al. ..... 340/286.07
8,548,548 B2 10/2013 Al-Ali
8,548,549 B2 10/2013 Schurman et al.
8,548,550 B2 10/2013 Al-Ali et al.
8,554,297 B2 10/2013 Moon et al.
8,560,032 B2 10/2013 Al-Ali et al.
8,560,034 B1 10/2013 Diab et al.
8,570,167 B2 10/2013 Al-Ali
8,570,503 B2 10/2013 Vo et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,581,732 B2 11/2013 Al-Ali et al.
8,584,345 B2 11/2013 Al-Ali et al.
8,588,880 B2 11/2013 Abdul-Hafiz et al.
8,600,467 B2 12/2013 Al-Ali et al.
8,606,342 B2 12/2013 Diab
8,626,255 B2 1/2014 Al-Ali et al.
8,630,691 B2 1/2014 Lamego et al.
8,634,889 B2 1/2014 Al-Ali et al.
8,641,631 B2 2/2014 Sierra et al.
8,652,060 B2 2/2014 Al-Ali
8,663,107 B2 3/2014 Kiani
8,666,468 B1 3/2014 Al-Ali
8,667,967 B2 3/2014 Al-Ali et al.
8,670,811 B2 3/2014 O'Reilly
8,670,814 B2 3/2014 Diab et al.
8,676,286 B2 3/2014 Weber et al.
8,682,407 B2 3/2014 Al-Ali
RE44,823 E 4/2014 Parker
RE44,875 E 4/2014 Kiani et al.
8,690,799 B2 4/2014 Telfort et al.
8,700,112 B2 4/2014 Kiani
8,702,627 B2 4/2014 Telfort et al.
8,706,179 B2 4/2014 Parker
8,712,494 B1 4/2014 MacNeish, III et al.
8,715,206 B2 5/2014 Telfort et al.
8,718,735 B2 5/2014 Lamego et al.
8,718,737 B2 5/2014 Diab et al.
8,718,738 B2 5/2014 Blank et al.
8,720,249 B2 5/2014 Al-Ali
8,721,541 B2 5/2014 Al-Ali et al.
8,721,542 B2 5/2014 Al-Ali et al.
8,723,677 B1 5/2014 Kiani
8,740,792 B1 6/2014 Kiani et al.
8,754,776 B2 6/2014 Poeze et al.
8,755,535 B2 6/2014 Telfort et al.

(56) References Cited

U.S. PATENT DOCUMENTS 8,755,856 B2 6/2014 Diab et al.
8,755,872 B1 6/2014 Marinow
8,761,850 B2 6/2014 Lamego
8,764,671 B2 7/2014 Kiani
8,768,423 B2 7/2014 Shakespeare et al.
8,771,204 B2 7/2014 Telfort et al.
8,777,634 B2 7/2014 Kiani et al.
8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,831,700 B2 9/2014 Schurman et al.
8,838,196 B2 9/2014 Mannheimer
8,840,549 B2 9/2014 Al-Ali et al.
8,847,740 B2 * 9/2014 Kiani et al. ..... 340/286.07
8,849,365 B2 9/2014 Smith et al.
8,852,094 B2 10/2014 Al-Ali et al.
8,852,115 B2 10/2014 Muir
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,909,310 B2 12/2014 Lamego et al.
8,911,377 B2 12/2014 Al-Ali
8,912,909 B2 12/2014 Al-Ali et al.
8,920,317 B2 12/2014 Al-Ali et al.
8,921,699 B2 12/2014 Al-Ali et al.
8,922,382 B2 12/2014 Al-Ali et al.
8,929,964 B2 1/2015 Al-Ali et al.
8,942,777 B2 1/2015 Diab et al.
8,948,834 B2 2/2015 Diab et al.
8,948,835 B2 2/2015 Diab
8,956,294 B2 2/2015 McCombie et al.
8,965,471 B2 2/2015 Lamego
8,983,564 B2 3/2015 Al-Ali
8,989,831 B2 3/2015 Ai-Ali et al.
8,996,085 B2 3/2015 Kiani et al.
8,998,809 B2 4/2015 Kiani
9,028,407 B1 * 5/2015 Bennett-Guerrero ..... A61B 5/1121 600/301
9,028,429 B2 5/2015 Telfort et al.
9,037,207 B2 5/2015 Al-Ali et al.
9,060,721 B2 6/2015 Reichgott et al.
9,066,666 B2 6/2015 Kiani
9,066,680 B1 6/2015 Al-Ali et al.
9,072,474 B2 7/2015 Al-Ali et al.
9,078,560 B2 7/2015 Schurman et al.
9,084,569 B2 7/2015 Weber et al.
9,095,316 B2 8/2015 Welch et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Al-Ali
9,119,595 B2 9/2015 Lamego
9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
9,153,112 B1 10/2015 Kiani et al.
9,153,121 B2 10/2015 Kiani et al.
9,161,696 B2 10/2015 Al-Ali et al.
9,161,713 B2 10/2015 Al-Ali et al.
9,167,995 B2 10/2015 Lamego et al.
9,176,141 B2 11/2015 Al-Ali et al.
9,186,102 B2 11/2015 Bruinsma et al.
9,192,312 B2 11/2015 Al-Ali
9,195,385 B2 11/2015 Al-Ali et al.
9,211,072 B2 12/2015 Kiani
9,211,095 B1 12/2015 Al-Ali
9,218,454 B2 12/2015 Kiani et al.
9,226,696 B2 1/2016 Kiani
9,241,662 B2 1/2016 Al-Ali et al.
9,245,668 B1 1/2016 Vo et al.
9,259,185 B2 2/2016 Abdul-Hafiz et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,928 B1 4/2016 Al-Ali et al.
9,323,894 B2 4/2016 Kiani
D755,392 S 5/2016 Hwang et al.
9,326,712 B1 5/2016 Kiani
9,333,316 B2 5/2016 Kiani
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-All et al.
9,375,185 B2 6/2016 Ali et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
9,408,542 B1 8/2016 Kinast et al.
9,436,645 B2 9/2016 Al-Ali et al.
9,445,759 B1 9/2016 Lamego et al.
9,466,919 B2 10/2016 Kiani et al.
9,474,474 B2 10/2016 Lamego et al.
9,192,329 B2 11/2016 Al-Ali
9,192,351 B1 11/2016 Telfort et al.
9,480,422 B2 11/2016 Al-Ali
9,480,435 B2 11/2016 Olsen
9,492,110 B2 11/2016 Al-Ali et al.
9,510,779 B2 12/2016 Poeze et al.
9,517,024 B2 12/2016 Kiani et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
9,591,975 B2 3/2017 Dalvi et al.
9,622,693 B2 4/2017 Diab
2002/0161291 A1 10/2002 Kianl et al.
2003/0137423 A1 7/2003 Al-Ali
2003/0191358 A1 10/2003 MacKin et al.
2004/0162499 A1 8/2004 Nagai et al.
2005/0027182 A1 * 2/2005 Siddiqui ..... A61B 5/14532 600/365
2005/0177096 A1 * 8/2005 Bollish ..... A61B 5/02055 604/65
2005/0240091 A1 10/2005 Lynn
2006/0220881 A1 * 10/2006 Al-Ali ..... A61B 5/14552 340/573.1
2007/0040692 A1 * 2/2007 Smith et al. ..... 340/573.1
2007/0282478 A1 12/2007 Al-Ali et al.
2008/0103375 A1 5/2008 Kiani ..... A61B 5/0002 600/323
2008/0244425 A1 10/2008 Kikin-Gil et al.
2008/0255438 A1 * 10/2008 Saidara ..... A61B 5/14532 600/365

(56) References Cited

U.S. PATENT DOCUMENTS

2008/0281168 A1* 11/2008 Gibson ..... A61B 5/0205 600/301
2009/0040874 A1* 2/2009 Rooney ..... A61J 7/0472 368/10
2009/0247848 A1 10/2009 Baker
2009/0247849 A1 10/2009 McCutcheon et al.
2009/0247984 A1 10/2009 Lamego et al.
2009/0275813 A1 11/2009 Davis
2009/0275844 A1 11/2009 Al-Ali
2010/0004518 A1 1/2010 Vo et al.
2010/0030040 A1 2/2010 Poeze et al.
2010/0113904 A1 5/2010 Batchelder et al.
2010/0331656 A1 12/2010 Mensinger et al.
2011/0082711 A1 4/2011 Poeze et al.
2011/0105854 A1 5/2011 Kiani et al.
2011/0125060 A1 5/2011 Telfort et al.
2011/0208015 A1 8/2011 Welch et al.
2011/0213212 A1 9/2011 Al-Ali
2011/0230733 A1 9/2011 Al-Ali
2011/0237969 A1 9/2011 Eckerbom et al.
2011/0288383 A1 11/2011 Diab
2012/0041316 A1 2/2012 Al-Ali et al.
2012/0046557 A1 2/2012 Kiani
2012/0059267 A1 3/2012 Lamego et al.
2012/0088984 A1 4/2012 Al-Ali et al.
2012/0105233 A1 5/2012 Bobey et al.
2012/0165629 A1 6/2012 Merritt et al.
2012/0209082 A1 8/2012 Al-Ali
2012/0209084 A1 8/2012 Olsen et al.
2012/0232366 A1* 9/2012 Kiani ..... A61B 5/1455 600/324
2012/0283524 A1 11/2012 Kiani et al.
2012/0296178 A1 11/2012 Lamego et al.
2012/0303085 A1 11/2012 Vitense et al.
2012/0319816 A1 12/2012 Al-Ali
2013/0023775 A1 1/2013 Lamego et al.
2013/0041591 A1 2/2013 Lamego
2013/0046204 A1 2/2013 Lamego et al.
2013/0060147 A1 3/2013 Welch et al.
2013/0096405 A1 4/2013 Garfio
2013/0096936 A1 4/2013 Sampath et al.
2013/0243021 A1 9/2013 Siskavich
2013/0253334 A1 9/2013 Al-Ali et al.
2013/0267804 A1 10/2013 Al-Ali
2013/0274572 A1 10/2013 Al-Ali et al.
2013/0296672 A1 11/2013 O'Neil et al.
2013/0296713 A1 11/2013 Al-Ali et al.
2013/0324808 A1 12/2013 Al-Ali et al.
2013/0331660 A1 12/2013 Al-Ali et al.
2013/0331670 A1 12/2013 Kiani
2014/0012100 A1 1/2014 Al-Ali et al.
2014/0034353 A1 2/2014 Al-Ali et al.
2014/0051953 A1 2/2014 Lamego et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0127137 A1 5/2014 Bellott et al.
2014/0129702 A1 5/2014 Lamego et al.
2014/0135588 A1 5/2014 Al-Ali et al.
2014/0142401 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0213864 A1 7/2014 Abdul-Hafiz et al.
2014/0266790 A1 9/2014 Al-Ali et al.
2014/0275808 A1 9/2014 Poeze et al.
2014/0275835 A1 9/2014 Lamego et al.
2014/0275871 A1 9/2014 Lamego et al.
2014/0275872 A1 9/2014 Merritt et al.
2014/0276115 A1 9/2014 Dalvi et al.
2014/0288400 A1 9/2014 Diab et al.
2014/0309507 A1 10/2014 Baker, Jr.
2014/0316217 A1 10/2014 Purdon et al.
2014/0316218 A1 10/2014 Purdon et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0330099 A1 11/2014 Al-Ali et al.
2014/0336481 A1 11/2014 Shakespeare et al.
2014/0357966 A1 12/2014 Al-Ali et al.
2015/0005600 A1 1/2015 Blank et al.
2015/0011907 A1 1/2015 Purdon et al.
2015/0012231 A1 1/2015 Poeze et al.
2015/0025406 A1 1/2015 Al-Ali
2015/0032029 A1 1/2015 Al-Ali et al.
2015/0038859 A1 2/2015 Dalvi et al.
2015/0045637 A1 2/2015 Dalvi
2015/0051462 A1 2/2015 Olsen
2015/0080754 A1 3/2015 Purdon et al.
2015/0087936 A1 3/2015 Al-Ali et al.
2015/0094546 A1 4/2015 Al-Ali
2015/0097701 A1 4/2015 Al-Ali et al.
2015/0099950 A1 4/2015 Al-Ali et al.
2015/0099951 A1 4/2015 Al-Ali et al.
2015/0099955 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0116076 A1 4/2015 Al-Ali et al.
2015/0126830 A1 5/2015 Schurman et al.
2015/0133755 A1 5/2015 Smith et al.
2015/0141781 A1 5/2015 Weber et al.
2015/0165312 A1 6/2015 Kiani
2015/0196237 A1 7/2015 Lamego
2015/0216459 A1 8/2015 Al-Ali et al.
2015/0230755 A1 8/2015 Al-Ali et al.
2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.
2015/0351697 A1 12/2015 Weber et al.
2015/0351704 A1 12/2015 Kiani et al.
2015/0359429 A1 12/2015 Al-Ali et al.
2015/0366472 A1 12/2015 Kiani
2015/0366507 A1 12/2015 Blank
2015/0374298 A1 12/2015 Al-Ali et al.
2015/0380875 A1 12/2015 Coverston et al.
2016/0000362 A1 1/2016 Diab et al.
2016/0007930 A1 1/2016 Weber et al.
2017/0007134 A1 1/2016 Al-Ali et al.
2016/0029932 A1 2/2016 Al-Ali
2016/0045118 A1 2/2016 Kiani
2016/0051205 A1 2/2016 Al-Ali et al.
2016/0058338 A1 3/2016 Schurman et al.
2016/0058347 A1 3/2016 Reichgott et al.
2016/0066823 A1 3/2016 Kind et al.
2016/0066824 A1 3/2016 Al-Ali et al.
2016/0066879 A1 3/2016 Telfort et al.
2016/0072429 A1 3/2016 Kiani et al.
2016/0081552 A1 3/2016 Wojtczuk et al.
2016/0095543 A1 4/2016 Telfort et al.
2016/0095548 A1 4/2016 Al-Ali et al.
2016/0103598 A1 4/2016 Al-Ali et al.
2016/0113527 A1 4/2016 Al-Ali et al.
2016/0143548 A1 5/2016 Al-Ali
2016/0166182 A1 6/2016 Al-Ali et al.
2016/0166183 A1 6/2016 Poeze et al.
2016/0166188 A1 6/2016 Bruinsma et al.
2016/0166210 A1 6/2016 Al-Ali
2016/0192869 A1 7/2016 Kiani et al.

(56) References Cited

U.S. PATENT DOCUMENTS

| | | | |
|---|---|---|---|
| 2016/0196388 | A1 | 7/2016 | Lamego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0007190 | A1 | 1/2017 | Al-Ali et al. |
| 2017/0007198 | A1 | 1/2017 | Al-Ali et al. |
| 2017/0014084 | A1 | 1/2017 | Al-Ali et al. |
| 2017/0021099 | A1 | 1/2017 | Al-Ali et al. |
| 2017/0027456 | A1 | 2/2017 | Kinast et al. |
| 2017/0042488 | A1 | 2/2017 | Muhsin |
| 2017/0055847 | A1 | 3/2017 | Kiani et al. |
| 2017/0055851 | A1 | 3/2017 | Al-Ali |
| 2017/0055882 | A1 | 3/2017 | Al-Ali et al. |
| 2017/0055887 | A1 | 3/2017 | Al-Ali |
| 2017/0055896 | A1 | 3/2017 | Al-Ali et al. |
| 2017/0079594 | A1 | 3/2017 | Telfort et al. |
| 2017/0086723 | A1 | 3/2017 | Al-Ali et al. |

OTHER PUBLICATIONS

Rheineck-Leyssius, MD, et al., "Advanced Pulse Oximeter Signal Processing Technology Compared to Simple Averaging. I. Effect on Frequency of Alarms in the Operating Room", Journal of Clinical Anesthesia, The Netherlands, May 1999, vol. 11, pp. 192-195.

Cust, Ae, et al., "Alarm settings for the Marquette 8000 pulse oximeter to prevent hyperoxic and hypoxic episodes", Journal Paediatric Child Health, 1999, vol. 35, pp. 159-162.

Lawless, Stephen T., "Crying wolf: False alarms in a pediatric intensive care unit", Critical Care Medicine, 1994, vol. 22, No. 6, pp. 981-985.

Informal Expert Report of Dr. Stephen Barker, Lead Case No. 16-05968-LT11, executed Feb. 10, 2017.

Impact of Clinical Alarms on Patient Safety, ACCE Healthcare Technology Foundation, 2006, 20 pages.

Taenzer, M.D., Andreas, "Impact of Pulse Oximetry Surveillance on Rescue Events and Intensive Care Unit Transfers", The American Society of Anesthesiologists, Inc., Feb. 2010, vol. 112, No. 2, pp. 282-287.

Stefanescu, MD MSc, Beatrice, "Improved Filtering of Pulse Oximeter Monitoring Alarms in the Neonatal ICU: Bedside Significance", Respiratory Care, Jan. 2016, vol. 61, No. 1, pp. 85-89.

Rheineck-Leyssius, A.T., et al., "Influence of pulse oximeter lower alarm limit on the incidence of hypoxaemia in the recovery room", British Journal of Anaesthesia, 1997, vol. 79, pp. 460-464.

Rheineck-Leyssius, MD, Aart, et al., "Influence of Pulse Oximeter Settings on the Frequency of Alarms, and Detection of Hypoxemia", Journal of Clinical Monitoring and Computing, 1998, vol. 14, pp. 151-156.

Pan, MD., Peter, "Intraoperative Pulse Oximetry: Frequency and Distribution of Discrepant Data", Journal of Clinical Monitoring and Computing, Nov./Dec. 1994, vol. 6, pp. 491-495.

Graham, Kelly, et al., Monitor Alarm Fatigue: Standardizing Use of Physiological Monitors and Decreasing Nuisance Alarms, American Journal of Critical Care, Jan. 2010, vol. 19, No. 1, pp. 27-37.

Barker, PhD, MD, Steven, "'Motion-Resistant' Pulse Oximetry: A Comparison of New and Old Models" Department of Anesthesiology, 2002, vol. 95, pp. 967-972.

National Patient Safety Goals Effective Jan. 1, 2015, Hospital Accreditation Program, The Joint Commission, Jan. 2015, pp. 1-17.

Brostowicz, Heather, et al. Oxygen saturation monitoring in the Neonatal Intensive Care Unit (NICU): Evaluation of a new alarm management, Journal of Neonatal-Perinatal Medicine 3, 2010, pp. 135-139.

Kowalczyk, Liz, "Patient alarms often unheard, unheeded" The Boston Globe, Feb. 13, 2011, in 5 pages.

Taenzer, Andreas, et al., "Postoperative Monitoring—The Dartmouth Experience", The Official Journal of the Anesthesia Patient Safety Foundation, Spring-Summer 2012, vol. 27, No. 1, pp. 1-28.

Tobin, Martin, "Principles and Practice of Intensive Care Monitoring", 1998, in 30 pages.

Severinghaus, M.D., John, et al., Pulse Oximeter Failure Thresholds in Hypotension and Vasoconstriction, Anesthesiology, Sep. 1990, vol. 73, No. 3, pp. 532-537.

Pologe, Jonas A., "Pulse Oximetry: Technical Aspects of Machine Design", International Anesthesiology Clinics, Advances in Oxygen Monitoring, Fall, 1987, vol. 25, No. 3, pp. 137-153.

Tremper, Ph.D., Kevin et al., "Pulse Oximetry", Medical Intelligence Article, Anesthesiology, Jan. 1989, vol. 70, No. 1, pp. 98-108.

Bosque, PhD, Elena, "Symbiosis of nurse and machine through fuzzy logic: Improved specificity of a neonatal pulse oximeter alarm", Dec. 1995, vol. 18, Issue 2, pp. 67-75.

Paine, MPH, Christine, et al., "Systematic review of physiologic monitor alarm characteristics and pragmatic interventions to reduce alarm frequency" J Hosp Med., Feb. 2017, vol. 11, No. 2, pp. 136-144.

Top 10 Technology Hazards for 2012, Guidance Article, Nov. 2011, www.ecri.org, pp. 358-373.

Top 10 Technology Hazards for 2013, Health Devices, ECRI Institute, Nov. 2012, reprinted from vol. 41, Issue 11, in 25 pages.

Top 10 Health Technology Hazards for 2014, Health Devices, ECRI Institute, Nov. 2013, www.ecri.org/2014hazards, 1 page.

Masimo Advanced Alarm Performance: An Evidence-Based Approach to Reduce False Alarms and Nuisance Alarms, 2010, in 8 pages.

International Search Report for PCT/US2009/052146, dated Dec. 15, 2009.

International Preliminary Report on Patentability and Written Opinion for PCT/US2009/052146 dated Feb. 10, 2011.

* cited by examiner

ALARM SUSPEND SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This [application] is *an application for reissue of U.S. Pat. No. 9,153,121, issued on Oct. 6, 2015 and titled "Alarm Suspend System," which is* a continuation of U.S. patent application Ser. No. 14/036,496, filed Sep. 25, 2013 and titled "Alarm Suspend System," which is a continuation of U.S. patent application Ser. No. 13/476,725, filed May 21, 2012 and titled "Alarm Suspend System," which is a continuation of U.S. patent application Ser. No. 12/510,982 filed Jul. 28, 2009 and titled "Alarm Suspend System," which claims priority benefit under 35 U.S.C. §119(e) to U.S. Provisional Patent Application Ser. No. 61/084,615, filed Jul. 29, 2008, titled "Alarm Management System[.];" *more than one reissue application has been filed for the reissue of U.S. Pat. No. 9,153,121, including U.S. patent application Ser. No. 15/583,935 (the present application), U.S. patent application Ser. No. 15/583,922, and U.S. patent application Ser. No. 15/583,948.* All of the above-referenced applications are hereby incorporated by reference herein in their entireties.

BACKGROUND

Pulse oximetry for measuring constituents of circulating blood has achieved acceptance in a wide variety of medical applications, including surgical wards, intensive care and neonatal units, general wards, home care, physical training, and virtually all types of monitoring scenarios. A pulse oximeter generally includes a two-wavelength optical sensor applied to a patient, a monitor for processing sensor signals and displaying results and a patient cable electrically interconnecting the sensor and the monitor. The monitor typically provides a numerical readout of physiological parameters such as oxygen saturation ($SpO_2$) and pulse rate (PR). Advanced physiological monitors utilize multiple wavelength sensors and enhanced measurement capabilities to provide readouts of additional parameters, such as carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785 and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate (PR), perfusion index (PI), pleth variability index (PVI), signal quality, HbCO and HbMet among other parameters are also available from Masimo.

SUMMARY OF THE INVENTION

Monitor alarms are triggered by out-of-limit parameters and system failures, the latter including monitor or sensor failures or improper sensor placement, to name a few. Alarms can be visual, audible or both. Alarms can also have different levels of priority, which are reflected in the type of visual and audible alarms. In an embodiment, parameters exceeding limits such as low $SpO_2$, high HbCO, high HbMet and low and high BPM trigger high priority alarms. System failures due to sensor off, no sensor or defective sensor also trigger high priority alarms. Parameters exceeding limits such as high $SpO_2$, low and high PI, low and high PVI, for example, trigger medium priority alarms. Parameters exceeding limits such as low HbCO and low HbMet along with a system low battery indication are examples of low priority alarms.

An audible alarm may be temporarily suspended by pressing an alarm silence button so as to prevent unnecessary disturbance to the patient and distraction of the caregiver. During alarm suspension, visual alarms remain active. If an alarm condition persists after a predetermined alarm suspend period, the audible alarm resumes. The alarm suspend period is typically long enough to give a caregiver sufficient time to intervene with appropriate patient treatment yet short enough to ensure that patient health is not endangered if intervention is ineffective. For conventional pulse oximetry, an alarm suspend may be, for example, a maximum of 120 seconds.

Alarm suspension on advanced blood parameter monitors is problematic. With conventional pulse oximetry, treatment for abnormal parameter measurements can be quickly applied and a patient response is typically fast. For example, a treatment for low oxygen saturation is the application of an oxygen mask or an increase in oxygen flow. By contrast, the duration of treatment for parameters measured by advanced monitors is highly dependent on the alarm-triggering parameter. For example, the treatment for high methemoglobin is the injection of methylene blue, and the patient response to such an injection is slow. When patient treatment time exceeds the maximum alarm suspend period, an audible alarm will constantly reactivate. Thus, a single alarm suspend duration for all parameters is inadequate to cope with the many different types of parameters measured by advanced monitors.

One aspect of an alarm suspend system for silencing the alarms is an alarm trigger responsive to any of various parameters and predetermined limits corresponding to the parameters, where the parameters are partitioned according to treatment time, i.e. the relative length of time it takes for a person to respond to medical treatment for a parameter measurement outside of the predetermined limits. An audible alarm is responsive to the alarm trigger. An alarm silence button is actuated so as to suspend the audible alarm. A timer tracks the duration of the suspended alarm and is initiated by actuation of an alarm silence button. The timer retriggers the audible alarm after the timed duration has lapsed/expired. In an embodiment, a long duration suspend time is associated with slow treatment parameters and a short duration suspend time is associated with fast treatment parameters. Fast treatment parameters may include, for example, parameters relating to normal blood hemoglobin constituents and slow treatment parameters may include parameters relating to abnormal blood hemoglobin constituents.

In various embodiments, a short duration suspend time is less than or equal to about two minutes and a long duration suspended time is greater than about two minutes. A default duration associated with the fast treatment parameters is about two minutes and a default duration associated with the slow treatment parameters is about fifteen minutes. The alarm suspend system may also have an alarm suspend override responsive to a predetermined unit change in the parameter triggering a suspended alarm. The override results in reactivation of the suspended alarm. A physiological monitor having an alarm suspend system may also have a pop-up window that appears on the monitor display in response to actuation of the silence button, where the pop-up window presents a choice of alarm suspend durations.

Another aspect of an alarm suspend system is a partition of measured parameters into at least a first group and a second group. An audible alarm is triggered if at least one parameter is outside of predetermined limits. The audible alarm is suspended in response to a silence request. A first duration is associated with the first group and a second duration is associated with the second group. The audible alarm is reactivated after at least one of the first duration and the second duration. The first duration may be set so as to generally correspond to a first range of treatment times for the first group of parameters. Likewise, the second duration may be set so as to generally correspond to a second range of treatment times for the second group of parameters, where the first range of treatment times and the second range of treatment times are non-overlapping.

In various embodiments, suspended audible alarms are overridden if the triggering parameter has greater than a predetermined unit change before the suspended alarm expires according to either the first duration or the second duration. The first and second groups are defined in relation to normal hemoglobin measurements abnormal hemoglobin measurements, respectively. The first duration is set to be less than or equal to two minutes and the second duration is set to be greater than two minutes, with default durations of about two minutes corresponding to the first group and about fifteen minutes corresponding to the second group. In an embodiment, a pop-up window for a monitor display is constructed and the first duration and the second duration are selected from a range of durations presented within the pop-up window.

A further aspect of an alarm suspend system deactivates an audible alarm for one of a short duration and a long duration according to the alarm-triggering parameter. A first group of parameters is associated with the short duration and a second group of parameters is associated with the long duration. The first group and the second group are partitioned according to a fast treatment time and a short treatment time associated with the parameters. An override reactivates the audible alarm if the trigger parameter changes more than a predetermine amount during the corresponding duration. In various embodiments, the first group comprises parameters related to the measurement of normal hemoglobin and the second group comprises parameters related to the measurement of abnormal hemoglobin. The long duration is greater than about 120 seconds and the short duration is less than or equal to about 120 seconds. A pop-up window for the display allows selection of the long duration and the short duration in response to the silence button.

DETAILED DESCRIPTION

Figure 1:
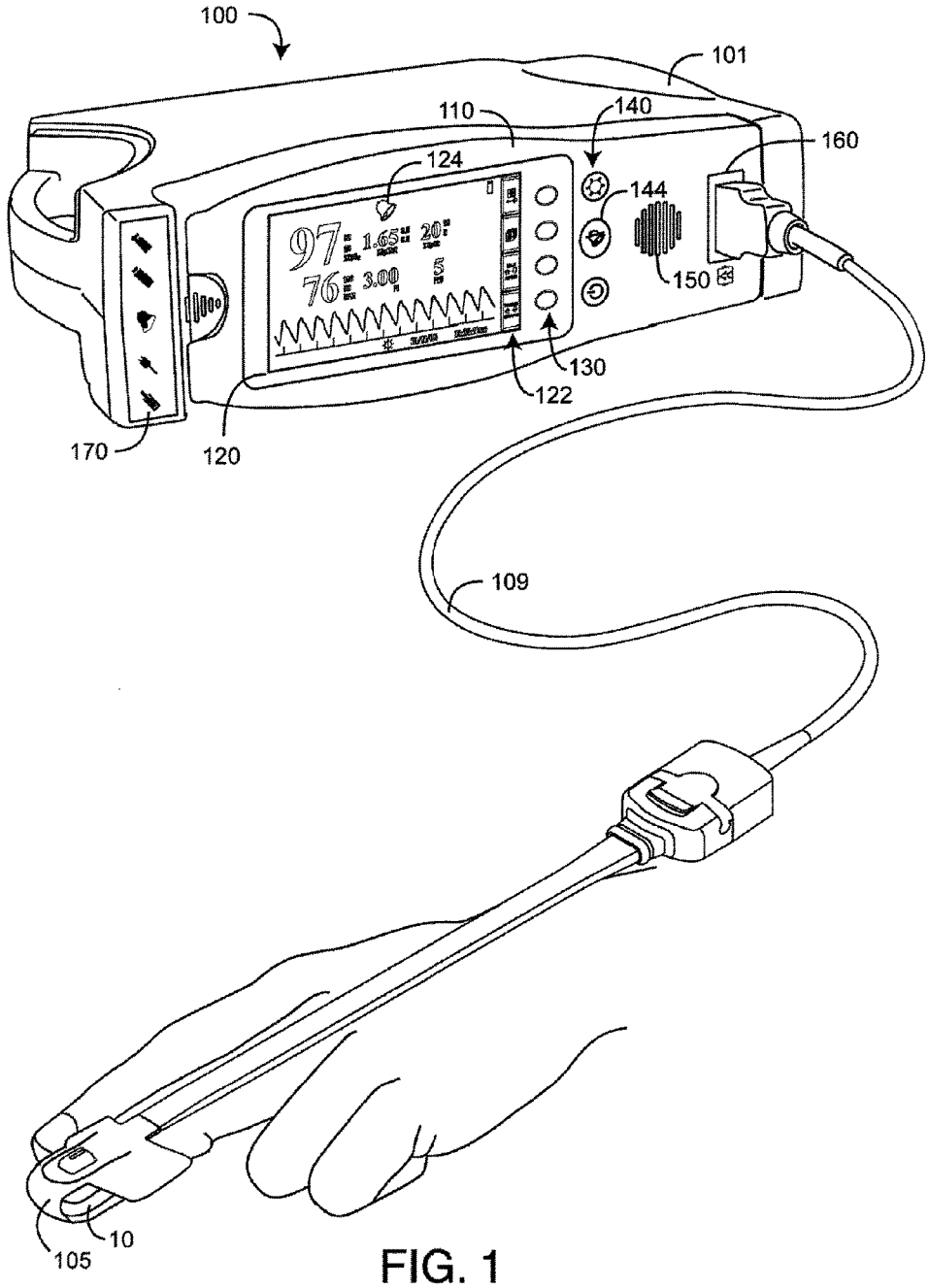
FIG. 1 is a perspective view of a physiological measurement system utilizing an alarm suspend system.

FIG. 1 illustrates a physiological measurement system 100 that utilizes an alarm suspend system. The physiological measurement system 100 has a noninvasive sensor 105 attached to a tissue site 10, a physiological monitor 101, and an interface cable 109 interconnecting the monitor 101 and the sensor 105. The physiological measurement system 100 may incorporate pulse oximetry in addition to advanced features, such as a multiple wavelength sensor and advanced processes for determining physiological parameters other than or in addition to those of pulse oximetry, such as carboxyhemoglobin, methemoglobin and total hemoglobin, as a few examples.

The monitor 101 has a front panel 110 providing a display 120, touch keys 130, controls 140, a speaker 150, a sensor port 160 and status indicators 170. The display 120 shows parameter readouts, limits and waveforms among other items. The display 120 also has touch key icons 122 that indicate touch key 130 functions. The speaker 150 provides an audible alarm in response to physiological measurements that violate preset conditions, such as an out-of-limit parameter, as well as system failures, such as a low battery condition. The controls 140 include an alarm silence button 144 that is pressed to temporarily suspend out-of-limit parameter alarms and system alarms, such as low battery. The display 120 provides visual alarms, which include a bell-shaped alarm status indicator 124 that illuminates during an alarm condition and parameter readouts 210 and limits 220 that flash when parameters are out-of-limit. Status indicators 170 also provide visual alarms. When there are multiple alarm conditions, the parameter displays 202 indicate parameters with the highest alarm priority. Touch keys 130 and corresponding icons 122 include an alarm menu access button for setting alarm conditions, such as high or low alarm limits for $SpO_2$, HbCO, HbMet, PR and PI. The alarm silence button 144 is pressed to temporarily suspend audible alarms. Advantageously, an alarm suspend system provides a parameter-dependent variation in the alarm suspend duration, as described below, utilizing a common silence button or other suspend initiator.

Figure 2:
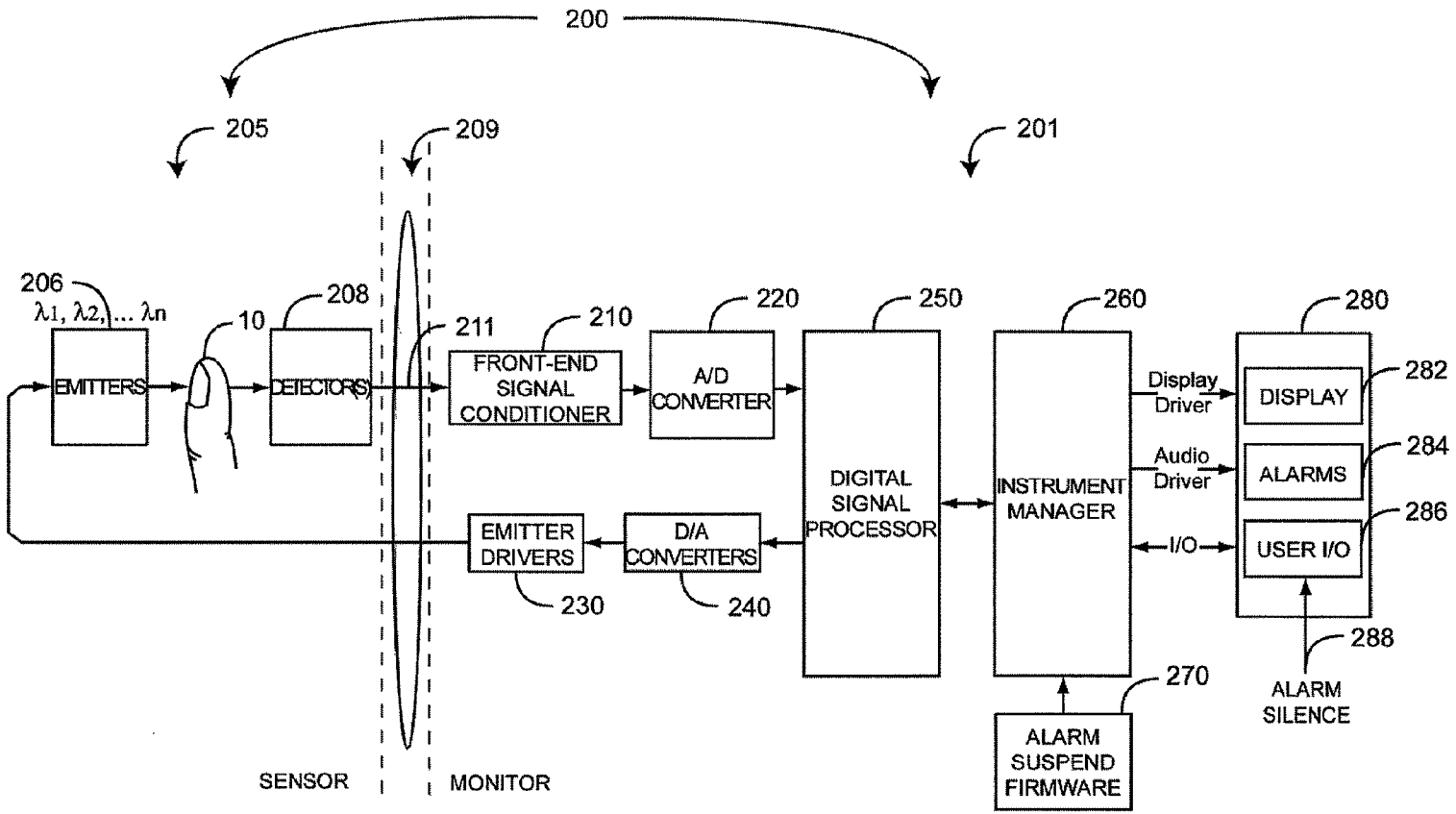
FIG. 2 is a detailed block diagram of a physiological measurement system utilizing an alarm suspend system.

FIG. 2 illustrates a physiological measurement system 200 including a physiological monitor 201, a sensor 205 and an interface cable 209. The sensor 205 is attached to a tissue site, such as a finger 10, and includes a plurality of emitters 206 irradiating the tissue site 10 with multiple wavelengths of light. The sensor 205 also includes one or more detectors 208 capable of detecting the light after attenuation by the tissue site 10. The sensor 205 transmits optical radiation at wavelengths other than or including the red and infrared wavelengths utilized in pulse oximeters. The monitor 201 inputs a corresponding sensor signal 211 and determines the relative concentrations of blood constituents other than or in addition to the "normal" blood hemoglobin constituents $HbO_2$ and Hb, including "abnormal" blood hemoglobin constituents HbCO, HbMet and blood related parameters such as fractional oxygen saturation, total hemoglobin and blood glucose to name a few.

As shown in FIG. 2, the monitor 201 has a front-end signal conditioner 210, an A/D converter 220, emitter drivers 230, D/A converters 240 and a digital signal processor ("DSP") 250. In general, the emitter drivers 230 convert digital control signals, via the D/A converters 240, into analog drive signals capable of driving the sensor emitters 206. The front-end signal conditioner 210 converts, via the A/D converter 220, composite analog intensity signal(s) from light sensitive detector(s) 208 into digital data input to the DSP 250. The emitter drivers 230 and front-end signal conditioner 210 communicate with the sensor 205 via the interface cable 209.

Also shown in FIG. 2, the monitor 201 has an instrument manager 260 and a user interface 280. The user interface 280 includes one or more displays 282, alarms 284 and user input/output (I/O) 286. The instrument manager 260 communicates with the DSP 250 to receive parameter data and to present that data on the display 282. The instrument manager 260 may also store and display historical or trending data related to one or more of the measured parameters or combinations of the measured parameters. The instrument manager 260 also controls audible and visual alarms and indicators 284. The instrument manager 260 responds to user-actuated keys and communicates with external devices via various I/O ports 286. Further, the instrument manager 260 executes alarm suspend firmware 270 so as to respond to an alarm silence button press 288, as described in detail with respect to FIGS. 3-4.

Figure 3:
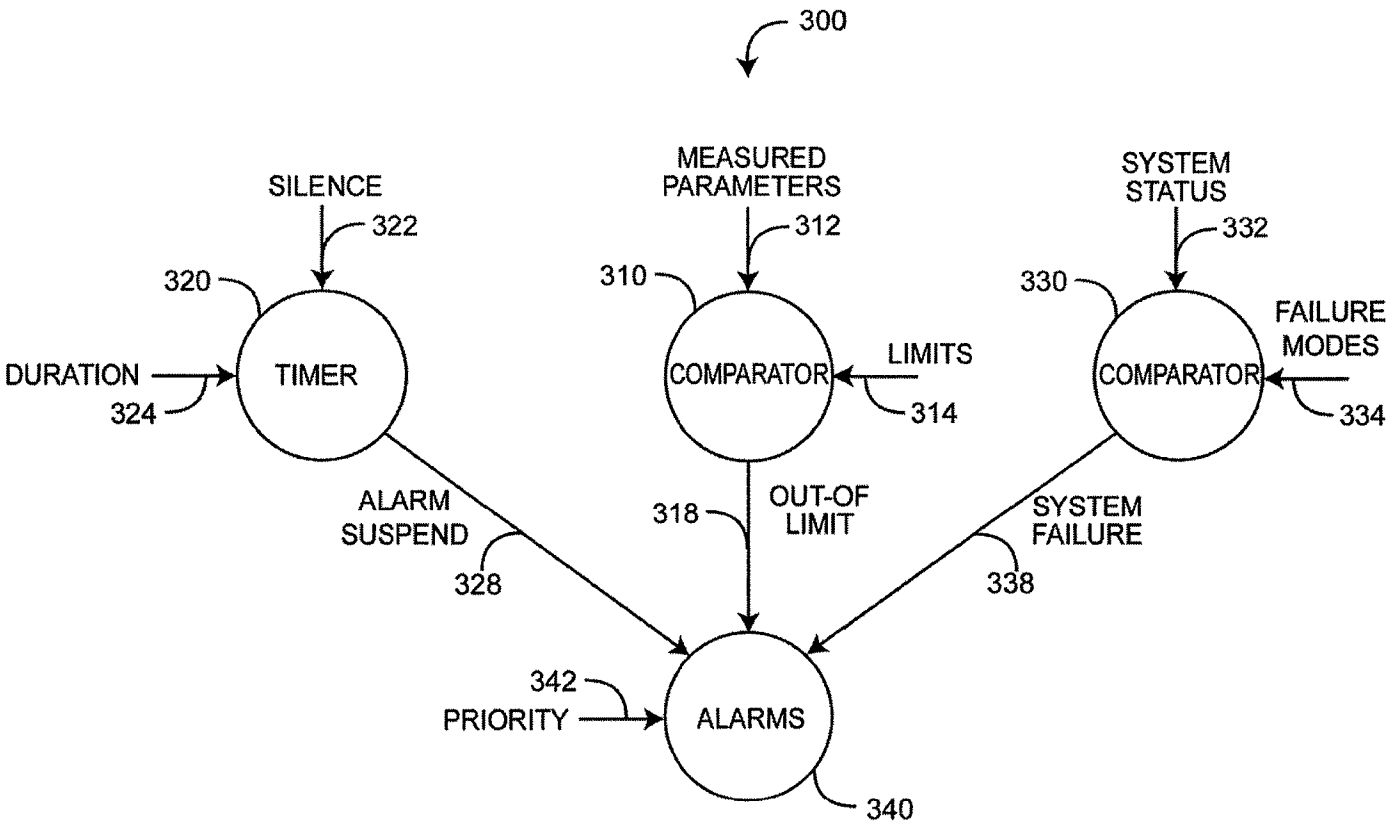
FIG. 3 is a flow diagram of an alarm suspend system embodiment.

FIG. 3 generally illustrates an alarm suspend system 300. Alarm triggers include system failures 338 and out-of-limit parameters 318. Triggered alarms 340 may be audible, visual or both, and may vary according to priority 342. Audible alarms may be generated by a monitor front-panel-mounted speaker 150 (FIG. 1) and may vary in loudness, pitch and sound pattern. Visual alarms may include parameter labels, parameter numerics, symbols and status lights, which can flash and vary in color.

As shown in FIG. 3, measured parameters 312 are compared 310 to default or user-specified limits 314. An out-of-limit condition 318 triggers an alarm 340. An alarm suspend 328 is user-initiated by a silence request 322. This may be a press of a silence button 144 (FIG. 1) on a monitor front panel 110 (FIG. 1). In an embodiment, the alarm suspend 328 silences audible alarms and modifies the display of visual alarms. The alarm suspend 328 is based on a timer 320, which ends the alarm suspend 328 after a predetermined duration 324. The duration 324 may be a function of the out-of-limit parameter 312. In an advantageous embodiment, the duration 324 relates to, or is a function of, the treatment time for the alarm-triggering parameter so as to avoid nuisance alarms while maintaining alarm integrity.

Figure 4:
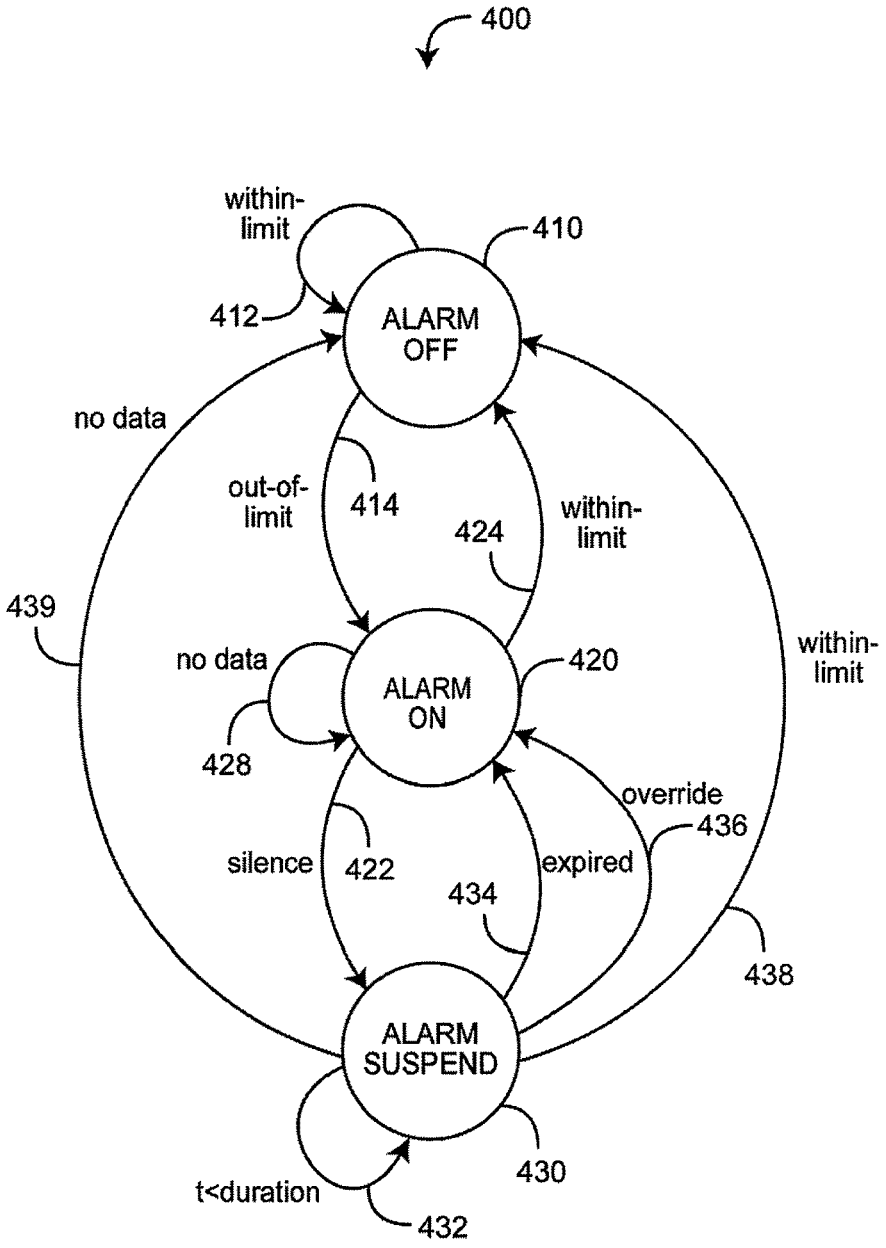
FIG. 4 is a state diagram of an alarm suspend system embodiment.

FIG. 4 illustrates an alarm suspend embodiment 400 that operates independently for each measured parameter that can trigger an alarm. An alarm is initially off 410. The alarm remains off as long as the parameter is within its set limits 412. If a parameter is measured outside of its set limits 414, an alarm is triggered 420. The alarm may audible, visual or both audible and visual. A user can request to silence the alarm by pressing an alarm silence button 144 (FIG. 1), for example. The silence request 422 suspends the alarm 430 which turns off audible alarms but, in an embodiment, does not deactivate visual alarms. The audible alarm remains suspended 430 for a predetermined duration 432. When the suspend duration has passed, the alarm suspend expires 434 and audible alarms are once again activated 420. The alarm remains on 428 until the triggering parameter is within limits 424 or a user once again requests silence 422. The alarm suspend 430 deactivates if the measured parameter becomes within limits 438, such as when the patient condition improves, or if no physiological data is detected 439, such as no sensor, sensor off, no cable or malfunctioning sensor situations, to name a few. Also, if the measured parameter changes during the alarm suspend 430 by a sufficient out-of-limit amount, an override 436 reactivates the audible alarms 420.

In an alarm suspend system embodiment, parameters are classified according to the typical time it takes for medical treatment to transition an out-of-limit measurement to a within-limit measurement. Suspend durations 324 (FIG. 3) are set accordingly. For example, in a two-tier embodiment, relatively slow treatment parameters, such as HbMet, HbCO, Hbt and PVI, are assigned relatively long suspend durations. Similarly, relatively fast treatment parameters, such as $SpO_2$ and PR, are assigned relatively short suspend durations. In an embodiment, the alarm suspend duration is adjustable for each individual parameter, including 2, 5, 10, 15, 20, 25 and 30 minutes for slow treatment parameters, with a default of 15 minutes; and 30, 60, 90 and 120 seconds for fast treatment parameters, with a default of 120 seconds. These alarm features are only active when alarm limits have been set. Other alarm features apply to both slow treatment and fast treatment parameters. For example, an alarm delay of 0, 5, 10 or 15 seconds applies to all enabled parameters.

In an embodiment, an override 436 occurs if slow treatment parameters such as HbCO, HbMet or PVI increase or Hbt decreases by a certain unit change during the alarm suspend duration. The unit change is adjustable for each parameter, such as from 1-15 in increments of 1. TABLE 1 shows a default embodiment of override unit changes for these parameters.

TABLE 1

Override Unit Changes for Selected Parameters

| Parameter | Unit Change | Direction |
|---|---|---|
| HbCO | 5 | Increase |
| HbMet | 2 | Increase |
| Hbt | 2 | Decrease |
| PVI | OFF | Increase |

Figure 5:
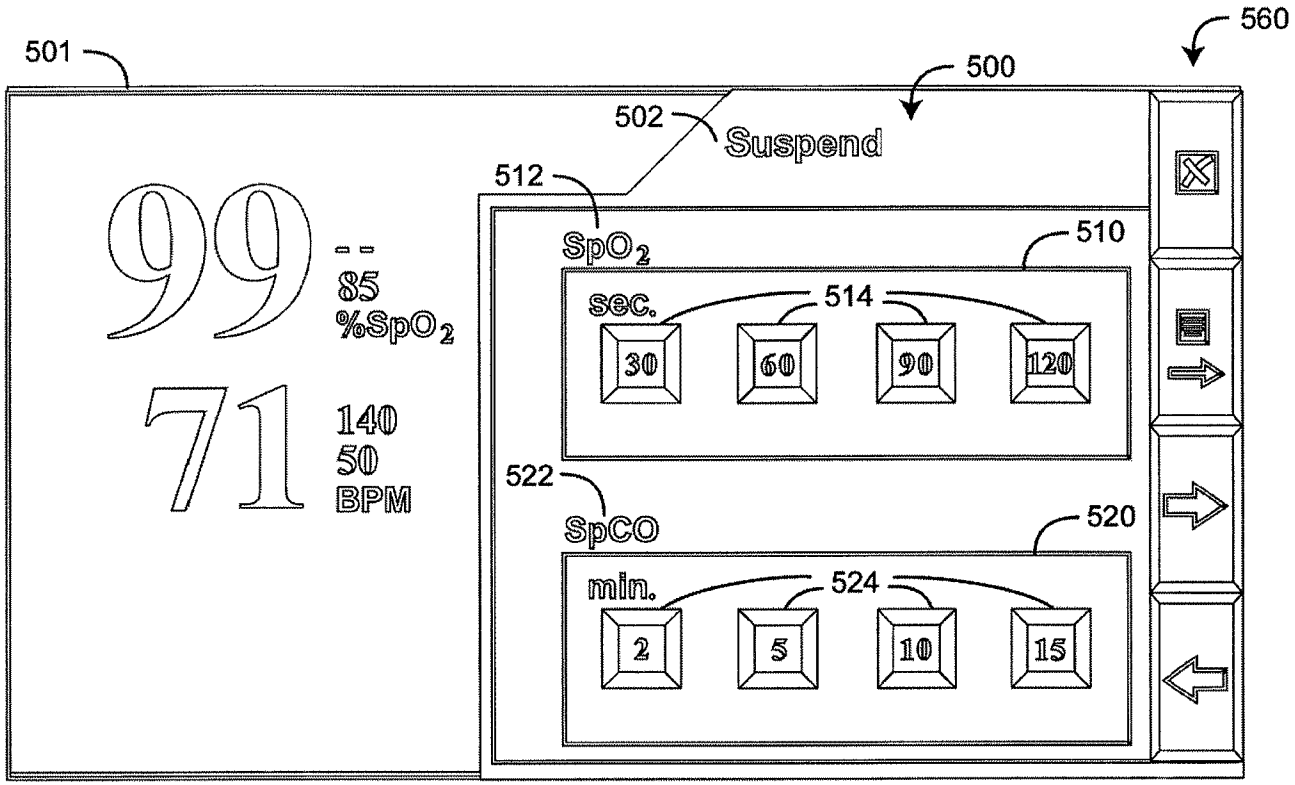
FIG. 5 is an illustration of an alarm suspend pop-up window.

FIG. 5 illustrates an alarm suspend window 500 that provides a "pop-up" display so that a monitor user may manually enter an alarm suspend duration. The alarm suspend window 500 appears as a portion of a monitor display 501, such as the front panel display 120 (FIG. 1) described above. The pop-up window 500 responds to a suspend request, such as a silence button 144 (FIG. 1) press. The alarm suspend window 500 has a window identifier 502 and one or more parameter subsections 510, 520. Each parameter subsection 510, 520 has a parameter identifier 512, 522 and corresponding suspend duration options 514, 524. In an embodiment, specific suspend times are selected via monitor touch keys 130 (FIG. 1) as guided by corresponding touch key icons 560. Selected suspend times are highlighted or otherwise identified and entered, also via a touch key 130 (FIG. 1). In an alternative embodiment, the monitor display is a touch screen and alarm suspend times are directly entered by a finger press on a specific duration "virtual button" 514, 524. Once one or more suspend durations are entered, the pop-up window 500 disappears from the display 501. The alarm suspend window 500 advantageously allows a user to quickly choose an appropriate alarm suspend duration for the situation at hand, rather than relying on a predetermined or default duration.

An alarm suspend system is described above with respect to alarms triggered by measured parameters and limits associated with those measured parameters. Limits may correspond to levels of a measured parameter, such as a percentage oxygen saturation to name but one example. Limits may also correspond to trends of a measured parameter, such as a rate-of-change of oxygen saturation, for example. Limits may also correspond to patterns in a measured parameter or a comparison of one measured parameter with another measured parameter, as further examples.

An alarm suspend system is described above with respect to a two-tier grouping of parameters, such as slow treatment and fast treatment parameters and alarm suspend durations associated with those groups. Groupings of parameters with respect to alarm suspend durations may be multi-tier, such as slow, medium and fast treatment parameters, to name but one example.

An alarm suspend system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological measurement system comprising:

a *noninvasive* physiological sensor [including: a plurality of light emitting diodes] configured to [transmit wavelengths of light onto a tissue site of a patient; and at least one detector configured to measure an indication of the wavelengths of light after attenuation by tissue of the patient and] *be positioned on a patient and* output a signal responsive [of the attenuated light] *to a physiological condition of the patient*; and one or more processors in communication with the *noninvasive* physiological sensor, the one or more processors configured to *electronically*:

*process the signal;*

*responsive to processing the signal,* determine a measurement of a physiological parameter based at least in part upon the signal;

*determine that the measurement of the physiological parameter satisfies an alarm activation threshold;*

[receive, from a user, an indication of] *initiate* a parameter-specific alarm *delay or* suspension period of time corresponding to the physiological parameter, the parameter-specific alarm *delay or* suspension period of time being [selected from] *one of* a plurality of parameter-specific alarm *delay or* suspension periods of time, the parameter-specific alarm *delay or* suspension period of time being different from at least one other parameter-specific alarm *delay or* suspension period of time corresponding to at least one other physiological parameter *for which the one or more processors are configured to determine at least one measurement*; [activate an alarm in response to determining that an alarm activation threshold has been satisfied by the physiological parameter measurement; receive an alarm suspension indication;] and

[in response to receiving the alarm suspension indication, suspend the alarm for] *activate an alarm for the physiological parameter in response to expiration of an amount of delay or suspension associated with* the [indicated] parameter-specific alarm *delay or* suspension period of time.

2. The physiological measurement system of claim 1, wherein the one or more processors are further configured to:

provide a user interface to the user including at least a plurality of user-selectable elements, each of the [selectable] *plurality of user-selectable* elements corresponding to one of the plurality of parameter-specific alarm *delay or* suspension periods of time.

3. The physiological measurement system of claim 2, wherein providing the user interface further includes:

constructing a pop-up window for a display; and displaying the plurality of user-selectable elements in the pop-up window.

4. The physiological measurement system of claim 3, wherein the plurality of user-selectable elements are configured to allow a user to select a specific one of the plurality of parameter-specific alarm *delay or* suspension periods of time.

5. The physiological measurement system of claim 4, wherein [the] *a* selected parameter-specific alarm *delay or* suspension period of time is selected by selection of one of the plurality of user-selectable elements.

6. The physiological measurement system of claim 1, wherein the one or more processors are further configured to:

associate [the] *a* selected parameter-specific *alarm delay or suspension* period of time [is] with the physiological parameter.

7. The physiological measurement system of claim 6, wherein the selected parameter-specific *alarm delay or suspension* period of time is stored in a memory device in communication with the one or more processors.

8. The physiological measurement system of claim 1, wherein the one or more processors are further configured to:

*responsive to processing the signal,* determine a *measurement of a* second physiological parameter [measurement] based at least in part upon the signal;

*determine that the measurement of the second physiological parameter satisfies a second alarm activation threshold;*

[receive, from the user, a second indication of] *initiate* a second parameter-specific alarm *delay or* suspension period of time corresponding to the second physiological parameter, the second parameter-specific alarm *delay or* suspension period of time being [selected from] *one of* a second plurality of parameter-specific alarm *delay or* suspension periods of time; [activate a second alarm in response to determining a second alarm activation threshold has been satisfied by the second physiological parameter measurement;] and

[in response to receiving the alarm suspension indication, suspend the second alarm for] *activate a second alarm for the second physiological parameter in response to expiration of an amount of delay or suspension asso-*

*ciated with* the [indicated] second parameter-specific alarm *delay or* suspension period of time.

9. The physiological measurement system of claim 8, wherein the one or more processors are further configured to:

provide a user interface to the user including at least a first plurality of user-selectable elements and a second plurality of user-selectable elements, wherein each of the first plurality of user-selectable elements corresponds to one of the plurality of parameter-specific alarm *delay or* suspension periods of time, and each of the second plurality of user-selectable element corresponds to one of the second plurality of parameter-specific alarm *delay or* suspension periods of time.

10. The physiological measurement system of claim 9, wherein the one or more processors are further configured to:

construct a pop-up window for a display; and display both the first and second plurality of user-selectable elements in the pop-up window.

11. The physiological measurement system of claim 10, wherein [the] *a* selected parameter-specific alarm *delay or* suspension period of time is selected by selection of one of the first plurality of user-selectable elements, and [the] *a* selected second parameter-specific alarm *delay or* suspension period of time is selected by selection of one of the second plurality of user-selectable elements.

12. The physiological measurement system of claim 11, wherein the at least one of the first plurality of parameter-specific alarm *delay or* suspension periods of time is different from any of the second plurality of parameter-specific alarm *delay or* suspension periods of time.

13. [An] *A* method *of electronically delaying or suspending an alarm while an electronically calculated measurement of a physiological parameter satisfies an alarm activation threshold, the measurement of the physiological parameter responsive to a signal from a noninvasive sensor positioned at a monitored patient, the method* comprising:

*electronically processing a signal from a noninvasive sensor;*

[measuring] *responsive to processing the signal, electronically determining a first measurement of* a *first* physiological parameter *and a second measurement of a second physiological parameter* using a patient monitoring device, the patient monitoring device including a processor and a memory device [configured to store]*;*

*electronically storing, using the patient monitoring device,* a *first* parameter-specific alarm *delay or* suspension period of time *corresponding to the first physiological parameter and a second parameter-specific alarm delay or suspension period of time corresponding to the second physiological parameter, the first parameter-specific alarm delay or suspension period of time being different from the second parameter-specific alarm delay or suspension period of time*;

*electronically determining, using the patient monitoring device, that the first measurement of the first physiological parameter satisfies a first alarm activation threshold;*

[receiving, from a user, an indication of a] *electronically initiating, using the patient monitoring device, the first* parameter-specific alarm *delay or* suspension period of time [corresponding to the physiological parameter, the parameter-specific alarm suspension period of time being selected from a plurality of parameter-specific alarm suspension periods of time, the parameter-specific alarm suspension period of time being different from at least one other parameter-specific alarm suspension period of time corresponding to at least one other physiological parameter; activating an alarm in response to determining an alarm activation threshold has been satisfied by the physiological parameter measurement; receiving an alarm suspension indication]; and

[in response to receiving the alarm suspension indication, suspending the alarm for] *electronically activating, using the patient monitoring device, a first alarm for the first physiological parameter in response to expiration of a first amount of delay or suspension associated with* the [indicated] *first* parameter-specific alarm *delay or* suspension period of time.

14. The method of claim 13, wherein the *first* alarm includes an audible component and a visual component, and wherein [suspending] *activating* the *first* alarm *in response to expiration of the first amount of delay or suspension* comprises [suspending] *activating* the audible component [and not suspending the visual component].

15. The method of claim 13 further comprising:

providing a user interface to the user including at least a plurality of user-selectable elements, each of the [selectable] *plurality of user-selectable* elements corresponding to one of [the] *a* plurality of parameter-specific alarm *delay or* suspension periods of time,

*wherein the plurality of parameter-specific alarm delay or suspension periods of time comprise the first parameter-specific alarm delay or suspension period of time.*

16. The method of claim 15 further comprising:

constructing a pop-up window for a display; and displaying the plurality of user-selectable elements in the pop-up window.

17. The method of claim 16, wherein [the] *a* selected parameter-specific alarm *delay or* suspension period of time is selected by selection of one of the plurality of user-selectable elements.

18. A physiological measurement system comprising:

a physiological sensor means for outputting a signal responsive to a [noninvasive measurement of attenuated light transmitted through a tissue site] *physiological condition* of a patient;

*a memory configured to store a first alarm activation threshold;* and

[a processing means] *one or more processors* in communication with the physiological sensor means and configured to:

*process the signal;*

*responsive to processing the signal,* determine a *first* measurement of [a] *the first measured* physiological parameter based at least in part upon the signal;

[receive, from a user, an indication of] *initiate* a *first* parameter-specific alarm *delay or* suspension period of time corresponding to the *first measured* physiological parameter, [the parameter-specific alarm suspension period of time being selected from a plurality of parameter-specific alarm suspension periods of time,] the *first* parameter-specific alarm *delay or* suspension period of time being different from [at least one other] *a second* parameter-specific alarm *delay or* suspension period of time corresponding to [at least one other] *a second measured* physiological parameter *for which the one or more processors are configured to determine a second measurement*;

*delay or suspend activation of an alarm for the first measured physiological parameter for the first*

*parameter-specific alarm delay or suspension period of time while the first alarm activation threshold is satisfied by the measurement of the first measured physiological parameter; and*

*subsequent to delaying or suspending activation of the alarm for the first parameter-specific alarm delay or suspension period of time,* activate [an] *the* alarm in response to determining [an] *the first* alarm activation threshold [has been] *is* satisfied by the *first measurement of the first measured* physiological parameter [measurement; receive an alarm suspension indication; and in response to receiving the alarm suspension indication, suspend the alarm for the indicated parameter-specific alarm suspension period of time].

19. The physiological measurement system of claim 18, wherein the [processing means is] *one or more processors are* further configured to:

*responsive to processing the signal,* determine [a] *the* second [physiological parameter] measurement based at least in part upon the signal;

[receive, from the user, a second indication of a] *initiate the* second parameter-specific alarm *delay or* suspension period of time [corresponding to the second physiological parameter, the second parameter-specific alarm suspension period of time being selected from a second plurality of parameter-specific alarm suspension periods of time];

*delay or suspend activation of a second alarm for the second measured physiological parameter for the second parameter-specific alarm delay or suspension period of time while a second alarm activation threshold is satisfied by the second measurement; and*

*subsequent to delaying or suspending activation of the second alarm for the second parameter-specific alarm delay or suspension period of time,* activate [a] *the* second alarm [in response] *responsive* to determining [a] *that the* second alarm activation threshold [has been] *is* satisfied by the second [physiological parameter] measurement[; and in response to receiving the alarm suspension indication, suspend the second alarm for the indicated second parameter-specific alarm suspension period of time].

20. The physiological measurement system of claim 19, wherein the [processing means is] *one or more processors are* further configured to:

provide a user interface to the user including at least a first plurality of user-selectable elements and a second plurality of user-selectable elements, wherein each of the first plurality of user-selectable elements corresponds to one of [the] *a first* plurality of parameter-specific alarm *delay or* suspension periods of time, and each of the second plurality of user-selectable element corresponds to one of [the] *a* second plurality of parameter-specific alarm *delay or* suspension periods of time,

*wherein the first plurality of parameter-specific alarm delay or suspension periods of time comprise the first parameter-specific alarm delay or suspension period of time, and the second plurality of parameter-specific alarm delay or suspension periods of time comprise the second parameter-specific alarm delay or suspension period of time.*

21. The physiological measurement system of claim 20, wherein [the] *a* selected *first* parameter-specific alarm *delay or* suspension period of time is selected by selection of one of the first plurality of user-selectable elements, and [the] *a* selected second parameter-specific alarm *delay or* suspension period of time is selected by selection of one of the second plurality of user-selectable elements.

22. The physiological measurement system of claim 21, wherein at least one of the first plurality of parameter-specific alarm *delay or* suspension periods of time is different from any of the second plurality of parameter-specific alarm *delay or* suspension periods of time.

*23. The physiological measurement system of claim 1, wherein the alarm comprises an audible alarm.*

*24. The physiological measurement system of claim 1, wherein the one or more processors are further configured to:*

*determine that the measurement of the physiological parameter satisfies a second alarm activation threshold different from the alarm activation threshold; and*

*in response to determining that the measurement of the physiological parameter satisfies the second alarm activation threshold, activate the alarm for the physiological parameter prior to expiration of the amount of delay or suspension associated with the first parameter-specific alarm delay or suspension period of time.*

*25. The physiological measurement system of claim 1, wherein the one or more processors are further configured to:*

*determine that a measurement of a second physiological parameter satisfies a second alarm activation threshold; and*

*in response to determining the measurement of the second physiological parameter satisfies the second alarm activation threshold, activate an alarm for the second physiological parameter prior to expiration of the amount of delay or suspension associated with the first parameter-specific alarm delay or suspension period of time.*

*26. The physiological measurement system of claim 1, wherein the physiological parameter comprises an oxygen saturation, and the at least one other physiological parameter comprises a pulse rate.*

* * * * *